US012616498B2

(12) United States Patent
Gennai

(10) Patent No.: US 12,616,498 B2
(45) Date of Patent: May 5, 2026

(54) GUIDE DEVICE FOR CANNULAS FOR THE COLLECTION OF MICRO-FRAGMENTED SUBCUTANEOUS ADIPOSE TISSUE

(71) Applicant: SEFFILINE S.R.L., Bologna (IT)

(72) Inventor: Alessandro Gennai, Bologna (IT)

(73) Assignee: SEFFILINE S.R.L., Bologna (IT)

( * ) Notice: Subject to any disclaimer, the term of this patent is extended or adjusted under 35 U.S.C. 154(b) by 805 days.

(21) Appl. No.: 17/794,687

(22) PCT Filed: Dec. 14, 2020

(86) PCT No.: PCT/IT2020/050310
§ 371 (c)(1),
(2) Date: Jul. 22, 2022

(87) PCT Pub. No.: WO2021/149083
PCT Pub. Date: Jul. 29, 2021

(65) Prior Publication Data
US 2023/0037855 A1    Feb. 9, 2023

(30) Foreign Application Priority Data

Jan. 23, 2020    (IT) ........................ 102020000001276

(51) Int. Cl.
*A61B 17/34*        (2006.01)
*A61M 1/00*        (2006.01)
*A61M 5/46*        (2006.01)

(52) U.S. Cl.
CPC ......... *A61B 17/3403* (2013.01); *A61M 1/815* (2021.05); *A61M 1/89* (2021.05); *A61M 5/46* (2013.01); *A61B 2017/3407* (2013.01); *A61M 2202/08* (2013.01)

(58) Field of Classification Search
CPC ........ A61B 17/3403; A61B 2017/3407; A61B 10/0283; A61B 2017/3405; A61B 2090/033; A61B 2090/08021; A61M 1/815; A61M 1/89; A61M 5/46; A61M 2202/08; A61M 1/84; A61M 2209/08
See application file for complete search history.

(56) References Cited

U.S. PATENT DOCUMENTS 2,876,770 A * 3/1959 White ..................... A61M 5/46
                                                            604/232
2012/0123386 A1* 5/2012 Tsals ................... A61M 5/3287
                                                            604/506

FOREIGN PATENT DOCUMENTS

WO        2019/092647        5/2019

OTHER PUBLICATIONS

International Search Report filed in PCT/IT2020/050310 mailed Mar. 22, 2021.

* cited by examiner

*Primary Examiner* — Theodore J Stigell
(74) *Attorney, Agent, or Firm* — RANKIN, HILL & CLARK LLP

(57)        ABSTRACT

A guide device for cannulas for the collection of micro-fragmented subcutaneous adipose tissue includes a handle which has an axial cavity intended to house a syringe equipped with a collection cannula. The axial cavity has an open proximal end, an open distal end and a central axis. A lip protrudes cantilevered from the distal end at a distance from the central axis and from said cannula. An intermediate anti-flexion element of the cannula is arranged between the handle and the lip.

10 Claims, 2 Drawing Sheets

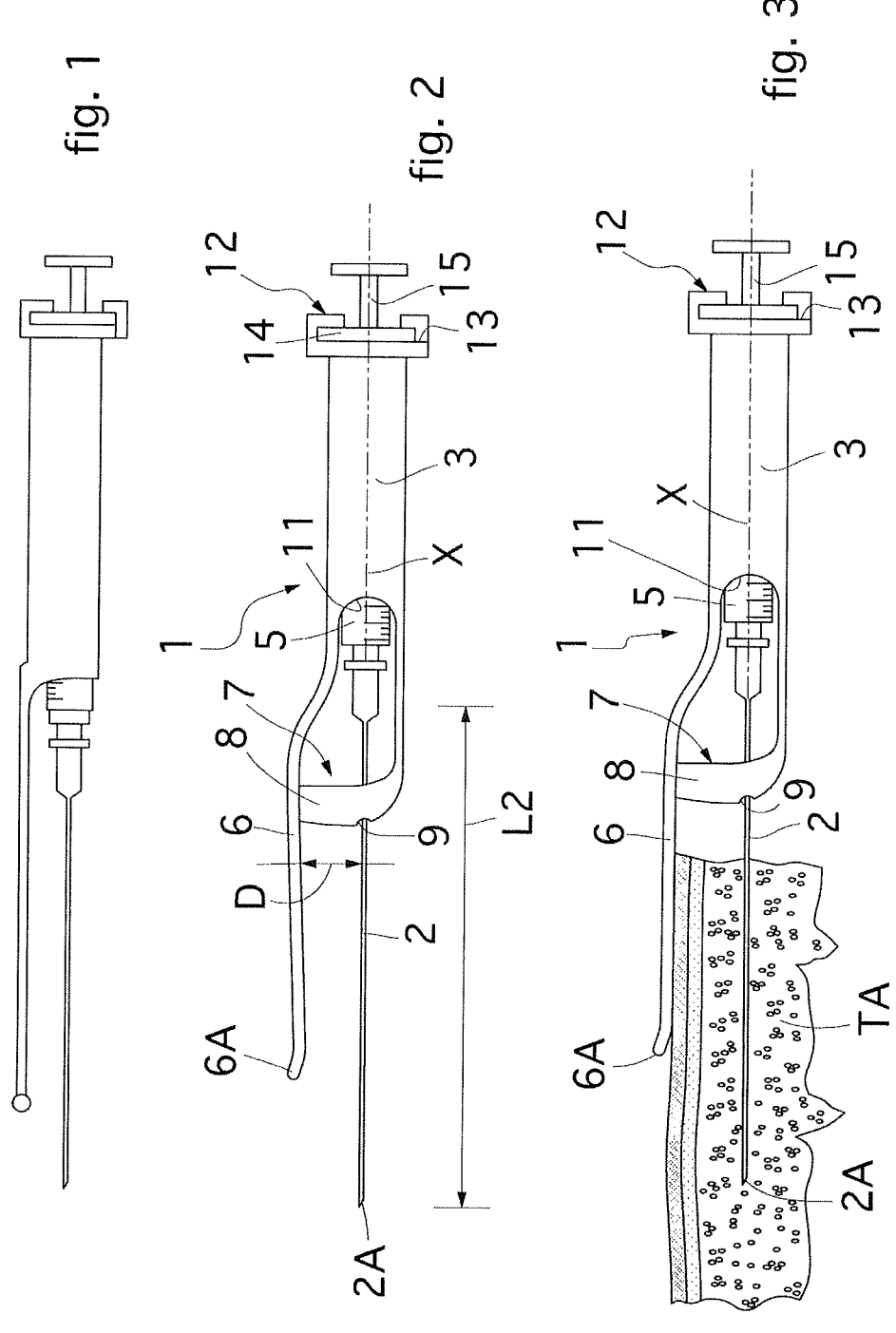

GUIDE DEVICE FOR CANNULAS FOR THE COLLECTION OF MICRO-FRAGMENTED SUBCUTANEOUS ADIPOSE TISSUE

FIELD OF THE INVENTION

The invention concerns a guide device for cannulas for the collection of micro fragmented subcutaneous adipose tissue, generally usable in the medical field to facilitate the maneuvers of physicians during the removal of adipose tissue from a patient.

BACKGROUND OF THE INVENTION

It is known that in some indications it is necessary to remove pre-determined volumes of adipose tissue from a patient.

In particular, adipose tissue can be removed both to exploit the properties of stromal vascular cells (SVF) and mesenchymal stem cells (ADSCs) naturally present in it, and also to perform liposuction operations.

According to the state of the art, in order to remove the adipose tissue, the physician uses a substantially rigid and beveled cannula which he/she introduces under the patient's skin in the removal zone after making a small incision.

The cannula is equipped with surface holes that communicate with an axial conduit and is grafted onto a syringe with which the physician, after having positioned it in the removal point, sucks out the established quantity of adipose tissue.

Typically, the positioning of the cannula is entrusted solely to the experience of the physician who has to introduce it under the skin in two steps, precisely an initial step in which, after making a small incision in the patient's epidermis, it passes through the skin in a substantially perpendicular direction, and a second step in which the physician rotates the cannula to arrange it substantially parallel to the surface of the skin and at such a depth as to meet the adipose tissue.

Both steps, of penetration and rotation, are fundamental for the safety of the patient and the effectiveness of the technique.

After introduction and positioning, the physician repeatedly performs some alternating movements, back and forth and fan-wise, and sucks out the adipose tissue with the syringe.

The cannula penetration step, as previously mentioned, is therefore extremely important, both to safeguard the patient's safety, avoiding plunging the cannula beyond the adipose tissue and risking damage to vital tissues and organs, and also to position the cannula at the right depth to then perform the rotation step and position the cannula parallel to the skin.

The correct depth is therefore the fundamental premise for the second, rotation step, in order to be able to perform the removal movements with maximum safety and with the certainty of reaching the adipose tissue which is the target of the removal.

To facilitate these two operating steps of the physician, the present Applicant has perfected a guide device that can be used to carry out a correct introduction and correct positioning of the cannula under the patient's skin.

The device consists of a handpiece that comprises a cylindrical body inside which a syringe can be housed on which a removal cannula is grafted.

A lip protrudes cantilevered from the cylindrical body which, in the operating step, is substantially parallel to the cannula, but kept at a predetermined distance from it.

Furthermore, the cannula extends by a predetermined length with respect to the end of the lip of the guide.

The distance between the cannula and the lip is substantially equal to the depth at which the subcutaneous adipose tissue has to be suctioned, while the length of the cannula that extends beyond the lip is the predetermined depth that has to be reached during the introduction of the cannula in order to prevent injury to tissues or deep vital organs.

In the introduction step, perpendicular to the skin, the lip of the guide acts as a stop to the excessive penetration of the cannula, while in the rotation step the lip is intended to rest externally on the skin and, during the forward and backward movement, it slides on it, maintaining the depth of the cannula under the skin constant.

The state of the art has a disadvantage which is that the cannula is supported completely cantilevered from the syringe and, therefore, also from the handpiece.

This circumstance, both during the introduction of the cannula under the patient's skin, and also during its movement in the steps of removing adipose tissue, causes flexion movements of the cannula with respect to the syringe and the handpiece held by the physician, and these flexions can make the positioning of the cannula inaccurate, generating the risk of not reaching the removal zone with precision or, even worse, of injuring the patient's internal organs not involved in the removal. In fact, the movement required for aspiration is both a "back and forth" and "fan-wise" movement.

The flexion of the cannula with respect to the attachment on the syringe can make the procedure extremely inaccurate and dangerous because, due to the flexion with respect to the attachment of the syringe, the cannula deviates from its axis which is no longer parallel to the external lip of the guide and this deviation can cause an error on the part of the operator who follows the external lip of the guide as an indicator for the position of the cannula under the skin.

PURPOSES OF THE INVENTION

One purpose of the invention is to overcome the disadvantage observed, making available a guide device for cannulas for the collection of micro-fragmented subcutaneous adipose tissue that allows to position the cannulas in the removal zone in a precise manner, and to keep such zone aligned with the lip of the guide during the "back and forth" and "fan-wise" movements used in the collection procedure.

Another purpose of the invention is to provide a guide device for cannulas for the collection of micro-fragmented subcutaneous adipose tissue that allows to visually check the quantities of adipose tissue collected.

According to one aspect of the invention, a guide device for cannulas for the collection of micro-fragmented subcutaneous adipose tissue is provided, in accordance with the characteristics of claim 1.

The invention allows to obtain the following advantages:
correctly position the cannulas without the occurrence of deviations caused by flexing of the cannulas during their insertion under the skin of the patients;
keep the cannula substantially integral with the guide during the execution of the "back and forth" and "fan-wise" movements;

constantly and visually check the quantities of adipose tissue collected.

BRIEF DESCRIPTION OF THE DRAWINGS

Other characteristics and advantages of the invention will become more apparent from the detailed description of some preferred, although not exclusive, embodiments of a guide device for cannulas for the collection of adipose tissue and stem cells derived from adipose tissue, given as a non-restrictive example in the attached drawings wherein:

FIG. 1 is a view of a known device for the collection of adipose tissue equipped with a collection cannula and syringe;

FIG. 2 is a view of the guide device for cannulas for the collection of adipose tissue and stem cells derived from adipose tissue according to the invention, equipped with a collection cannula and syringe;

FIG. 3 is a view of the device according to the invention in a schematic representation of use;

DETAILED DESCRIPTION OF AN EXAMPLE OF A PREFERRED EMBODIMENT

Figures 4, 5, 6:
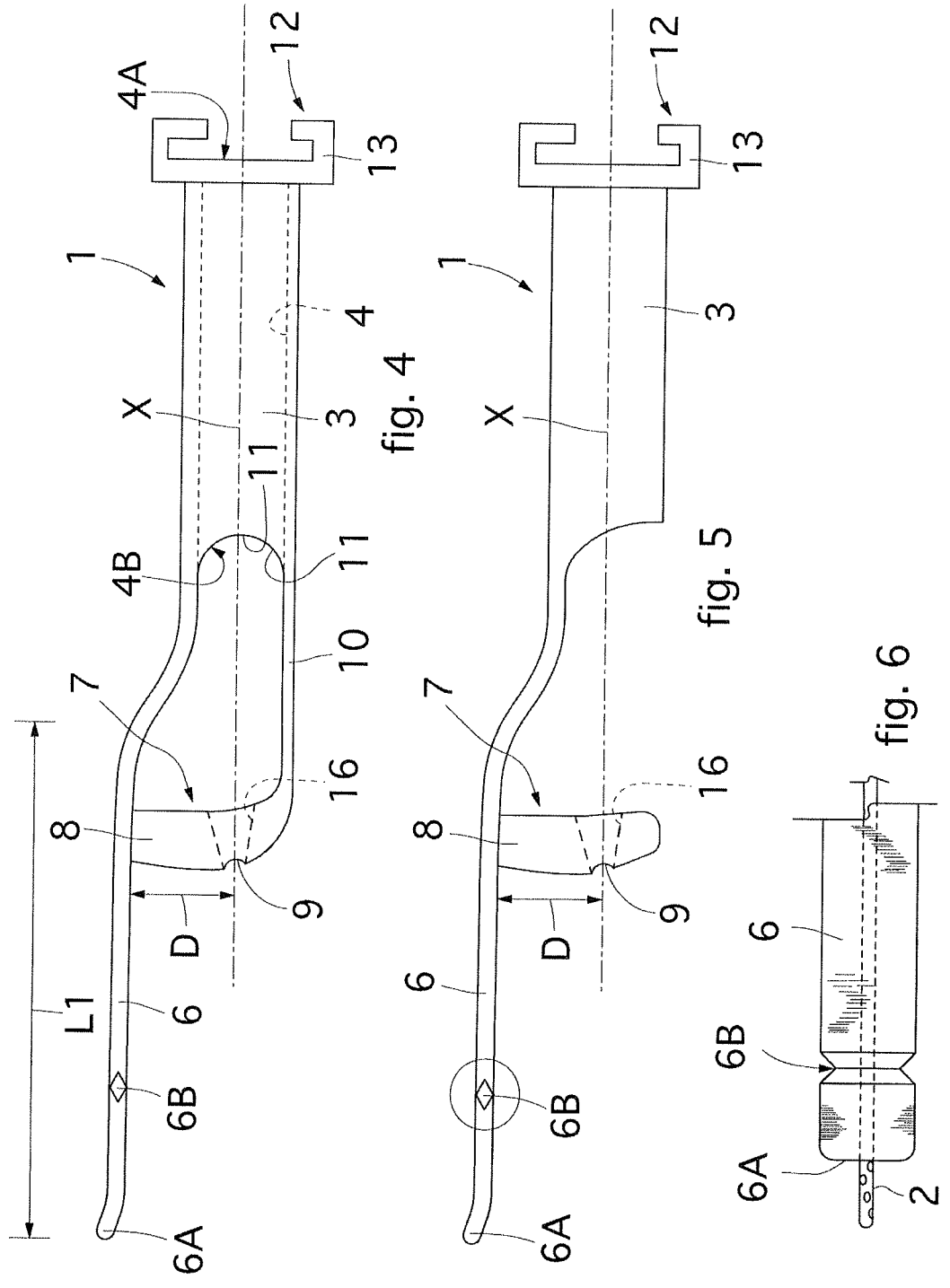
FIG. 4 is an enlarged scale view of the guide device for cannulas for the collection of adipose tissue and stem cells derived from adipose tissue, without the collection cannula and syringe.
FIG. 5 is a view of a second possible version of the guide device for cannulas for the collection of adipose tissue and stem cells derived from adipose tissue according to the invention.
FIG. 6 is a top view of a portion of the guide device according to the invention.

With reference to the drawings as above, 1 denotes as a whole a guide device for cannulas 2 for the collection of adipose tissue TA and stem cells derived from adipose tissue.

The guide device 1, hereafter device 1 for short, comprises a handle 3 which has an axial cavity 4 intended to house a syringe 5 equipped with a collection cannula 2.

The axial cavity 4 preferably has a cylindrical profile and has an open proximal end 4A, an open distal end 4B and a central axis X.

A cantilevered lip 6 extends from the distal end 4B, located at a distance D from the central axis X and, consequently, from the cannula 2.

An anti-flexion intermediate element 7 of the cannula 2 is arranged between the handle 3 and the lip 6.

The intermediate element 7 comprises a tooth 8 which projects transversely from the lip 6 toward the central axis X and has a through hole 9 intended to be passed through by at least one section of a cannula 2.

In a preferred embodiment of the device 1, the tooth 8 can comprise a connection segment 10 with the handle 3, in order to give the tooth 8 greater strength and stability.

The handle 3 can comprise at least one inspection window 11 to visually check the quantities of adipose tissue TA removed from a patient.

The inspection window 11 can be achieved by removing part of the material with which the handle 3 is made, or be made as a transparent portion, or the entire handle 3 can be made entirely of a transparent material.

The handle 3 comprises retention means 12 of the syringe 5 in the axial cavity 4 which comprise an interlocking profile 13 formed at the proximal end 4A and intended to be engaged with a peripheral portion of a syringe 5, specifically with the peripheral collar 14 which the latter typically have at the inlet end of their plunger 15.

The lip 6 has a length L1 which is shorter than the length L2 of a cannula 2, so that the tip 2A thereof protrudes with respect to the distal end 6A of the lip 6 which, preferably, is slightly curved outward, that is, in an opposite direction to the central X axis.

At a predetermined distance from the distal end 6A, the lip 6 has a reference point to allow a physician to visually assess, during the maneuvers for the collection of the adipose tissue TA, the length of the cannula section introduced under the patient's skin, so as to be able to perform the maneuvers with the maximum guarantee of not damaging the patient's internal organs.

This reference, in the preferred version, consists of a transverse notch 6B made in the lip 6, but the person of skill will understand that other types of references can be used on the device 1 for the same purpose.

In a possible embodiment of the device 1, the tooth 8 can have a lead-in flare 16 to facilitate the introduction and passing through of a cannula 2.

The functioning of the invention is as follows: when it is necessary to remove a quantity of adipose tissue from under the skin of a patient, the device 1 is prepared by mounting a syringe 5, preemptively equipped with a removal cannula 2 and inserting it inside the cavity 4 of the handle 3, from the open proximal end 4A.

In the insertion maneuver, the cannula 2 is made to slide through the tooth 8 by means of the through hole 9 and the insertion continues until the peripheral collar 14 of the syringe 5 rests on the edge of the proximal end 4A.

In order to clamp the syringe 5 in the position of use, it is rotated about its longitudinal axis (which practically coincides with the central axis X) in a clockwise or counterclockwise direction by an angle sufficient to make the collar 14 engage in the interlocking profile 13.

In this position, the cannula 2 protrudes with respect to the lip 6, since the length L1 of the latter is shorter than the length L2 of the cannula 2 and the distal end 2A of the cannula 2 is ready to pass through the patient's skin and reach the zone of removal of adipose tissue TA.

The difference between the length L2 of the cannula 2 that extends beyond the length L1 of the lip 6 corresponds to the predetermined depth that has to be reached under the patient's skin during the step of introducing the cannula 2.

During the known maneuvers of both insertion and also collection, the cannula 2 cannot flex because it is held axially by the tooth 8 which prevents deviations thereof from its normal rectilinear direction.

In this way, it is possible to direct the cannula 2 with maximum precision by referring to the lip 6 with which it remains aligned, without it being able to flex due, for example, to the resistance opposed by the patient's skin tissues.

Furthermore, the transverse notch 6B provides the physician with the exact length of the section of cannula 2 inserted under the patient's skin, so as to move the device 1 back and forth without the danger of excessively sinking the cannula 2 into the patient's tissues or, in reverse, accidentally extracting the cannula 2 therefrom.

When the cannula 6 is correctly positioned in the removal point, the adipose tissue TA is sucked out with the syringe 5 and it is possible to check through the window 11, or through the handle 3 if this is made completely transparent, the correct accumulation of the suctioned matter inside the syringe 5.

When the accumulation is completed, the syringe 5 is rotated about its longitudinal axis in the opposite direction to that of insertion and the collar 14 disengages from the interlocking profile 13, releasing the syringe loaded with adipose tissue TA and which can be removed from the cavity 4 of the handle 3, for the intended uses of the adipose tissue removed.

In practice, it has been verified that the invention achieves the intended purposes.

The invention as conceived is susceptible to modifications and variants, all of which are within the scope of the inventive concept.

Furthermore, all the details can be replaced with other technically equivalent elements.

In their practical embodiment, any other materials, as well as shapes and sizes, can be used according to requirements, without departing from the field of protection of the following claims.

The invention claimed is:

1. A guide device for a collection cannula for the collection of micro-fragmented subcutaneous adipose tissue, said guide device comprising:
  a handle which has an axial cavity configured to house a syringe equipped with the collection cannula, said axial cavity having an open proximal end, an open distal end and a central axis;
  a lip which protrudes cantilevered from said open distal end parallel to the collection cannula at a distance from said central axis and from said collection cannula;
  wherein the collection cannula extends by a predetermined length with respect to the end of the lip of the guide device, wherein an intermediate anti-flexion element for said collection cannula is arranged between said handle and said lip and wherein said intermediate anti-flexion element comprises a tooth which projects transversely from said lip toward said central axis and which has a through hole intended for the passage of at least a section of the collection cannula.

2. The device according to claim 1, wherein said tooth comprises a connection segment with said handle.

3. The device according to claim 1, further comprising at least one inspection window obtained in said handle.

4. The device according to claim 1, wherein said handle comprises a partially or totally transparent handle.

5. The device according to claim 1, wherein said axial cavity is a cylindrical cavity wherein the syringe equipped with the collection cannula can be precisely housed.

6. The device according to claim 1, wherein said handle comprises retention means of the syringe equipped with the collection cannula in said axial cavity.

7. The device according to claim 6, wherein said retention means comprise an interlocking profile obtained in said open proximal end and configured to be engaged with a peripheral portion of the syringe.

8. The device according to claim 1, wherein said lip has a length lower than a length of the collection cannula.

9. The device according to claim 1, wherein said lip has a free distal end curved in opposite direction with respect to said central axis.

10. The device according to claim 9, wherein said lip has a reference point obtained at a selected distance from said free distal end.

* * * * *